United States Patent
Rousson et al.

(10) Patent No.: US 11,484,652 B2
(45) Date of Patent: Nov. 1, 2022

(54) CLOSED-LOOP BLOOD GLUCOSE CONTROL SYSTEMS AND METHODS

(71) Applicant: DIABELOOP, Grenoble (FR)

(72) Inventors: Sylvain Rousson, Grenoble (FR); Romain Blanc, Grenoble (FR); Maeva Doron, Grenoble (FR)

(73) Assignee: DIABELOOP, Grenoble (FR)

( * ) Notice: Subject to any disclaimer, the term of this patent is extended or adjusted under 35 U.S.C. 154(b) by 390 days.

(21) Appl. No.: 16/645,436

(22) PCT Filed: Aug. 1, 2018

(86) PCT No.: PCT/EP2018/070901
§ 371 (c)(1),
(2) Date: Mar. 6, 2020

(87) PCT Pub. No.: WO2019/025506
PCT Pub. Date: Feb. 7, 2019

(65) Prior Publication Data
US 2020/0282141 A1 Sep. 10, 2020

(30) Foreign Application Priority Data
Aug. 2, 2017 (EP) .................................... 17306034

(51) Int. Cl.
*A61M 5/172* (2006.01)
*G16H 20/17* (2018.01)
*G16H 50/50* (2018.01)
*A61M 5/142* (2006.01)

(52) U.S. Cl.
CPC .......... *A61M 5/1723* (2013.01); *G16H 20/17* (2018.01); *G16H 50/50* (2018.01); *A61M 2005/14208* (2013.01); *A61M 2005/1726* (2013.01); *A61M 2205/3303* (2013.01); *A61M 2230/06* (2013.01); *A61M 2230/201* (2013.01)

(58) Field of Classification Search
None
See application file for complete search history.

(56) References Cited

U.S. PATENT DOCUMENTS

| | | |
|---|---|---|
| 6,368,141 B1 | 4/2002 | Vanantwerp et al. |
| 6,558,320 B1 | 5/2003 | Causey, III et al. |
| 6,641,533 B2 | 11/2003 | Causey, III et al. |
| 7,060,059 B2 | 6/2006 | Keith et al. |
| 7,204,823 B2 | 4/2007 | Estes et al. |

(Continued)

FOREIGN PATENT DOCUMENTS

| | | |
|---|---|---|
| WO | WO1998043700 A1 | 10/1998 |
| WO | WO1998043701 A1 | 10/1998 |

(Continued)

OTHER PUBLICATIONS

International Search Report issued in related PCT Application No. PCT/EP2018/070901 dated Sep. 21, 2018.

*Primary Examiner* — Manuel A Mendez (57) ABSTRACT

An automated closed-loop blood glucose control system comprises a continuous glucose-monitoring sensor (101), a subcutaneous insulin delivery device (103); and a controller (105) which determines a maximal allowable insulin injection amount and determines an insulin delivery control signal on the basis of the maximal allowable insulin injection amount and the quantity of insulin to inject.

14 Claims, 4 Drawing Sheets

(56) References Cited

U.S. PATENT DOCUMENTS

| | | |
|---|---|---|
| 7,402,153 B2 | 7/2008 | Steil et al. |
| 7,404,796 B2 | 7/2008 | Ginsberg |
| 7,491,187 B2 | 2/2009 | Van Den et al. |
| 7,547,281 B2 | 6/2009 | Hayes et al. |
| 7,651,489 B2 | 1/2010 | Estes et al. |
| 7,660,615 B2 | 2/2010 | Vanantwerp et al. |
| 7,766,830 B2 | 8/2010 | Fox et al. |
| 7,806,854 B2 | 10/2010 | Damiano et al. |
| 7,837,647 B2 | 11/2010 | Estes et al. |
| 7,887,511 B2 | 2/2011 | Mernøe et al. |
| 7,941,200 B2 | 5/2011 | Weinert et al. |
| 7,942,844 B2 | 5/2011 | Moberg et al. |
| 7,946,985 B2 | 5/2011 | Mastrototaro et al. |
| 8,012,119 B2 | 9/2011 | Estes et al. |
| 8,062,249 B2 | 11/2011 | Wilinska et al. |
| 8,192,395 B2 | 6/2012 | Estes et al. |
| 8,226,556 B2 | 7/2012 | Hayes et al. |
| 8,246,540 B2 | 8/2012 | Ginsberg |
| 8,273,052 B2 | 9/2012 | Damiano et al. |
| 8,337,469 B2 | 12/2012 | Eberhart et al. |
| 8,475,409 B2 | 7/2013 | Tsoukalis |
| 8,500,702 B2 | 8/2013 | Estes et al. |
| 8,562,587 B2 | 10/2013 | Kovatchev et al. |
| 8,568,357 B2 | 10/2013 | Ortega et al. |
| 8,579,879 B2 | 11/2013 | Palerm et al. |
| 8,585,593 B2 * | 11/2013 | Kovatchev ............. A61B 5/222 600/347 |
| 8,585,637 B2 | 11/2013 | Wilinska et al. |
| 8,594,118 B2 | 11/2013 | Cooper et al. |
| 8,622,991 B2 | 1/2014 | Pesach et al. |
| 8,679,016 B2 | 3/2014 | Mastrototaro et al. |
| 8,712,748 B2 | 4/2014 | Thukral et al. |
| 8,762,070 B2 | 6/2014 | Doyle, III et al. |
| 8,784,364 B2 | 7/2014 | Kamen et al. |
| 8,795,233 B2 | 8/2014 | Mernoe et al. |
| 8,870,763 B2 | 10/2014 | Yang et al. |
| 8,882,665 B2 | 11/2014 | Yang et al. |
| 9,022,996 B2 | 5/2015 | Eberhart et al. |
| 9,056,165 B2 | 6/2015 | Steil et al. |
| 9,089,305 B2 | 7/2015 | Hovorka |
| 9,244,077 B2 | 1/2016 | Yodfat et al. |
| 9,283,323 B2 | 3/2016 | Toumazou et al. |
| 9,295,777 B2 | 3/2016 | Mernoe et al. |
| 9,320,471 B2 | 4/2016 | Hayes et al. |
| 9,333,298 B2 | 5/2016 | Kim et al. |
| 9,345,426 B2 | 5/2016 | Colvin, Jr. et al. |
| 9,364,609 B2 | 6/2016 | Keenan et al. |
| 9,398,869 B2 | 7/2016 | Kovatchev et al. |
| 9,402,953 B2 | 8/2016 | Wilinska et al. |
| 9,414,775 B2 | 8/2016 | Colvin, Jr. et al. |
| 9,445,757 B2 | 9/2016 | Desborough et al. |
| 9,452,258 B2 | 9/2016 | Dobbles et al. |
| 9,452,259 B2 | 9/2016 | Dobbles et al. |
| 9,457,146 B2 | 10/2016 | Dobbles et al. |
| 9,463,277 B2 | 10/2016 | Dobbles et al. |
| 9,474,855 B2 | 10/2016 | Mccann et al. |
| 9,486,578 B2 | 11/2016 | Finan et al. |
| 9,504,785 B2 | 11/2016 | Forsell |
| 9,526,834 B2 | 12/2016 | Keenan et al. |
| 9,572,935 B2 | 2/2017 | Dobbles et al. |
| 9,572,936 B2 | 2/2017 | Dobbles et al. |
| 9,586,004 B2 | 3/2017 | Dobbles et al. |
| 9,597,453 B2 | 3/2017 | Dobbles et al. |
| 9,603,561 B2 | 3/2017 | Varsavsky et al. |
| 9,623,179 B2 | 4/2017 | Mastrototaro et al. |
| 9,636,453 B2 | 5/2017 | Monirabbasi et al. |
| 9,642,568 B2 | 5/2017 | Shah et al. |
| 9,649,058 B2 | 5/2017 | Varsavsky et al. |
| 9,649,059 B2 | 5/2017 | Varsavsky et al. |
| 9,662,445 B2 | 5/2017 | Parikh et al. |
| 9,669,160 B2 | 6/2017 | Harris et al. |
| 9,687,194 B2 | 6/2017 | Cantwell et al. |
| 9,750,438 B2 | 9/2017 | Kovatchev et al. |
| 9,757,510 B2 | 9/2017 | Finan |
| 9,795,737 B2 | 10/2017 | Finan et al. |
| 9,795,738 B2 | 10/2017 | Steil et al. |
| 9,827,372 B2 | 11/2017 | Dobbles et al. |
| 9,849,239 B2 | 12/2017 | Grosman et al. |
| 9,854,998 B2 | 1/2018 | Yang et al. |
| 9,867,930 B2 | 1/2018 | Kamen et al. |
| 9,872,959 B2 | 1/2018 | Yodat et al. |
| 9,878,096 B2 | 1/2018 | Roy et al. |
| 9,878,097 B2 | 1/2018 | Estes |
| 9,907,491 B2 | 3/2018 | Li et al. |
| 9,907,909 B2 | 3/2018 | Finan et al. |
| 9,943,256 B2 | 4/2018 | Varsavsky et al. |
| 9,943,645 B2 | 4/2018 | Monirabbasi et al. |
| 9,999,728 B2 | 6/2018 | Parikh et al. |
| 10,039,479 B2 | 8/2018 | Varsavsky et al. |
| 10,111,588 B2 | 10/2018 | Tankiewicz et al. |
| 10,117,992 B2 | 11/2018 | Parikh et al. |
| 10,130,767 B2 | 11/2018 | Grosman et al. |
| 10,154,804 B2 | 12/2018 | Steil et al. |
| 10,173,006 B2 | 1/2019 | Patek et al. |
| 10,188,793 B2 | 1/2019 | Mazlish |
| 10,194,839 B2 | 2/2019 | Staib et al. |
| 10,194,845 B2 | 2/2019 | Shah et al. |
| 10,252,002 B2 | 4/2019 | Haider et al. |
| 10,258,264 B2 | 4/2019 | Varsavsky et al. |
| 10,293,101 B2 | 5/2019 | Brewer et al. |
| 10,293,108 B2 | 5/2019 | Roy |
| 10,297,350 B2 | 5/2019 | Duke et al. |
| 10,332,632 B2 | 6/2019 | Duke et al. |
| 10,332,633 B2 | 6/2019 | Duke et al. |
| 10,357,606 B2 | 7/2019 | Rosinko et al. |
| 10,390,740 B2 | 8/2019 | Desborough et al. |
| 10,420,489 B2 | 9/2019 | Kovatchev et al. |
| 10,426,385 B2 | 10/2019 | Varsavsky et al. |
| 10,433,774 B2 | 10/2019 | Gottlieb et al. |
| 10,496,797 B2 | 12/2019 | Monirabbasi et al. |
| 10,507,284 B2 | 12/2019 | Doyle, III et al. |
| 2002/0002326 A1 | 1/2002 | James, III et al. |
| 2002/0119711 A1 | 8/2002 | Vanantwerp et al. |
| 2003/0114836 A1 | 6/2003 | Estes et al. |
| 2004/0068230 A1 | 4/2004 | Estes et al. |
| 2004/0152622 A1 | 8/2004 | Keith et al. |
| 2004/0193025 A1 | 9/2004 | Steil et al. |
| 2005/0096511 A1 | 5/2005 | Fox et al. |
| 2005/0096512 A1 | 5/2005 | Fox et al. |
| 2005/0113653 A1 | 5/2005 | Fox et al. |
| 2005/0171503 A1 | 8/2005 | Van Den et al. |
| 2005/0192494 A1 | 9/2005 | Ginsberg |
| 2005/0245878 A1 | 11/2005 | Mernoe et al. |
| 2005/0245904 A1 | 11/2005 | Estes et al. |
| 2007/0016127 A1 | 1/2007 | Staib et al. |
| 2007/0060869 A1 | 3/2007 | Tolle et al. |
| 2007/0223512 A1 | 9/2007 | Cooper et al. |
| 2007/0233019 A1 | 10/2007 | Forsell |
| 2007/0255125 A1 | 11/2007 | Moberg et al. |
| 2007/0255250 A1 | 11/2007 | Moberg et al. |
| 2007/0287985 A1 | 12/2007 | Estes et al. |
| 2008/0064944 A1 | 3/2008 | Vanantwerp et al. |
| 2008/0097289 A1 | 4/2008 | Steil et al. |
| 2008/0161664 A1 | 7/2008 | Mastrototaro et al. |
| 2008/0183060 A1 | 7/2008 | Steil et al. |
| 2008/0208113 A1 | 8/2008 | Damiano et al. |
| 2008/0269585 A1 | 10/2008 | Ginsberg |
| 2008/0269723 A1 | 10/2008 | Mastrototaro et al. |
| 2008/0319381 A1 | 12/2008 | Yodat et al. |
| 2009/0099506 A1 | 4/2009 | Estes et al. |
| 2009/0099509 A1 | 4/2009 | Estes et al. |
| 2009/0112076 A1 | 4/2009 | Estes et al. |
| 2009/0118664 A1 | 5/2009 | Estes et al. |
| 2009/0118665 A1 | 5/2009 | Estes et al. |
| 2009/0143662 A1 | 6/2009 | Estes et al. |
| 2009/0149803 A1 | 6/2009 | Estes et al. |
| 2009/0234213 A1 | 9/2009 | Hayes et al. |
| 2010/0004598 A1 | 1/2010 | Eberhart et al. |
| 2010/0057043 A1 | 3/2010 | Kovatchev et al. |
| 2010/0152644 A1 | 6/2010 | Pesach et al. |
| 2010/0179768 A1 | 7/2010 | Kovatchev et al. |
| 2010/0185142 A1 | 7/2010 | Kamen et al. |
| 2010/0198143 A1 | 8/2010 | Estes et al. |
| 2010/0249561 A1 | 9/2010 | Patek et al. |

(56) References Cited

U.S. PATENT DOCUMENTS

| | | |
|---|---|---|
| 2010/0280441 A1 | 11/2010 | Wilinska et al. |
| 2010/0324382 A1 | 12/2010 | Cantwell et al. |
| 2011/0009814 A1 | 1/2011 | Tsoukalis |
| 2011/0028901 A1 | 2/2011 | Estes et al. |
| 2011/0106049 A1 | 5/2011 | Damiano et al. |
| 2011/0137238 A1 | 6/2011 | Mernøe et al. |
| 2011/0208155 A1 | 8/2011 | Palerm et al. |
| 2011/0208156 A1 | 8/2011 | Doyle, III et al. |
| 2011/0218489 A1 | 9/2011 | Mastrototaro et al. |
| 2011/0257627 A1 | 10/2011 | Hovorka |
| 2011/0282320 A1 | 11/2011 | Steil et al. |
| 2011/0282321 A1 | 11/2011 | Steil et al. |
| 2011/0295341 A1 | 12/2011 | Estes et al. |
| 2011/0313390 A1 | 12/2011 | Roy et al. |
| 2012/0006100 A1 | 1/2012 | Gottlieb et al. |
| 2012/0010600 A1 | 1/2012 | Wilinska et al. |
| 2012/0035547 A1 | 2/2012 | Estes et al. |
| 2012/0041414 A1 | 2/2012 | Estes et al. |
| 2012/0041415 A1 | 2/2012 | Estes et al. |
| 2012/0059353 A1 | 3/2012 | Kovatchev et al. |
| 2012/0078067 A1 | 3/2012 | Kovatchev et al. |
| 2012/0123234 A1 | 5/2012 | Atlas et al. |
| 2012/0172694 A1 | 7/2012 | Desborough et al. |
| 2012/0220928 A1 | 8/2012 | Estes et al. |
| 2012/0259278 A1 | 10/2012 | Hayes et al. |
| 2013/0030358 A1 | 1/2013 | Yodfat Ofer et al. |
| 2013/0041343 A1 | 2/2013 | Toumazou et al. |
| 2013/0060105 A1 | 3/2013 | Shah et al. |
| 2013/0060106 A1 | 3/2013 | Aasmul et al. |
| 2013/0079613 A1 | 3/2013 | Kovatchev et al. |
| 2013/0079709 A1 | 3/2013 | Eberhart et al. |
| 2013/0102866 A1 | 4/2013 | Li et al. |
| 2013/0102867 A1 | 4/2013 | Desborough et al. |
| 2013/0109940 A1 | 5/2013 | Yang et al. |
| 2013/0109942 A1 | 5/2013 | Yang et al. |
| 2013/0274183 A1 | 10/2013 | Kim et al. |
| 2013/0298063 A1 | 11/2013 | Joy et al. |
| 2013/0331667 A1 | 12/2013 | Colvin, Jr. et al. |
| 2014/0005633 A1 | 1/2014 | Finan |
| 2014/0018644 A1 | 1/2014 | Colvin, Jr. et al. |
| 2014/0039383 A1 | 2/2014 | Dobbles et al. |
| 2014/0046159 A1 | 2/2014 | Kovatchev et al. |
| 2014/0052091 A1 | 2/2014 | Dobbles et al. |
| 2014/0052092 A1 | 2/2014 | Dobbles et al. |
| 2014/0052093 A1 | 2/2014 | Dobbles et al. |
| 2014/0052094 A1 | 2/2014 | Dobbles et al. |
| 2014/0052095 A1 | 2/2014 | Dobbles et al. |
| 2014/0066884 A1 | 3/2014 | Keenan et al. |
| 2014/0066885 A1 | 3/2014 | Keenan et al. |
| 2014/0066886 A1 | 3/2014 | Roy et al. |
| 2014/0066887 A1 | 3/2014 | Mastrototaro et al. |
| 2014/0066888 A1 | 3/2014 | Parikh et al. |
| 2014/0066889 A1 | 3/2014 | Grosman et al. |
| 2014/0066892 A1 | 3/2014 | Keenan et al. |
| 2014/0081236 A1 | 3/2014 | Wilinska et al. |
| 2014/0114278 A1 | 4/2014 | Dobbles et al. |
| 2014/0128803 A1 | 5/2014 | Dobbles et al. |
| 2014/0155679 A1 | 6/2014 | Pesach et al. |
| 2014/0163517 A1 | 6/2014 | Finan et al. |
| 2014/0180240 A1 | 6/2014 | Finan et al. |
| 2014/0200559 A1 | 7/2014 | Doyle, III et al. |
| 2014/0276419 A1 | 9/2014 | Rosinko et al. |
| 2014/0276554 A1 | 9/2014 | Finan et al. |
| 2014/0323957 A1 | 10/2014 | Mernoe et al. |
| 2014/0350359 A1 | 11/2014 | Tankiewicz et al. |
| 2015/0031973 A1 | 1/2015 | Yang et al. |
| 2015/0045767 A1 | 2/2015 | Kamen et al. |
| 2015/0066531 A1 | 3/2015 | Jacobson et al. |
| 2015/0100038 A1 | 4/2015 | Mccann et al. |
| 2015/0105644 A1 | 4/2015 | Yang et al. |
| 2015/0164383 A1 | 6/2015 | Varsavsky et al. |
| 2015/0164384 A1 | 6/2015 | Varsavsky et al. |
| 2015/0164385 A1 | 6/2015 | Varsavsky et al. |
| 2015/0164388 A1 | 6/2015 | Varsavsky et al. |
| 2015/0164389 A1 | 6/2015 | Varsavsky et al. |
| 2015/0190098 A1 | 7/2015 | Patek et al. |
| 2015/0238694 A1 | 8/2015 | Steil et al. |
| 2015/0352282 A1 | 12/2015 | Mazlish |
| 2016/0030669 A1 | 2/2016 | Harris et al. |
| 2016/0038673 A1 | 2/2016 | Morales |
| 2016/0106918 A1 | 4/2016 | Yodfat et al. |
| 2016/0158438 A1 | 6/2016 | Monirabbasi et al. |
| 2016/0158441 A1 | 6/2016 | Monirabbasi et al. |
| 2016/0162662 A1* | 6/2016 | Monirabbasi .......... G16H 10/40 604/504 |
| 2016/0199571 A1 | 7/2016 | Rosinko et al. |
| 2016/0228042 A9 | 8/2016 | Li et al. |
| 2016/0256629 A1 | 9/2016 | Grosman et al. |
| 2016/0317743 A1 | 11/2016 | Estes |
| 2016/0339175 A1 | 11/2016 | Yan et al. |
| 2016/0354019 A1 | 12/2016 | Desborough et al. |
| 2017/0049961 A1 | 2/2017 | Roy |
| 2017/0065212 A1 | 3/2017 | Gottlieb et al. |
| 2017/0076068 A1 | 3/2017 | Dobbles et al. |
| 2017/0080152 A1 | 3/2017 | Wilinska et al. |
| 2017/0087300 A1 | 3/2017 | Parikh et al. |
| 2017/0119961 A1 | 5/2017 | Forsell |
| 2017/0119968 A1 | 5/2017 | Keenan et al. |
| 2017/0143899 A1 | 5/2017 | Gondhalekar et al. |
| 2017/0150911 A1 | 6/2017 | Varsavsky et al. |
| 2017/0173261 A1 | 6/2017 | O'connor et al. |
| 2017/0189614 A1 | 7/2017 | Mazlish et al. |
| 2017/0203030 A1 | 7/2017 | Brewer et al. |
| 2017/0209080 A1 | 7/2017 | Varsavsky et al. |
| 2017/0209082 A1 | 7/2017 | Varsavsky et al. |
| 2017/0215775 A1 | 8/2017 | Shah et al. |
| 2017/0216518 A1 | 8/2017 | Davis et al. |
| 2017/0216524 A1 | 8/2017 | Haider et al. |
| 2017/0220750 A1 | 8/2017 | Davis et al. |
| 2017/0220751 A1 | 8/2017 | Davis et al. |
| 2017/0258986 A1 | 9/2017 | Tsoukalis |
| 2017/0281867 A1 | 10/2017 | Parikh et al. |
| 2017/0325736 A1 | 11/2017 | Cantwell et al. |
| 2017/0337348 A1 | 11/2017 | Kovatchev et al. |
| 2017/0348482 A1 | 12/2017 | Duke et al. |
| 2017/0348483 A1 | 12/2017 | Duke et al. |
| 2017/0348484 A1 | 12/2017 | Duke et al. |
| 2018/0043095 A1 | 2/2018 | Finan et al. |
| 2018/0043096 A1 | 2/2018 | Dobbles et al. |
| 2018/0133394 A1 | 5/2018 | Kamen et al. |
| 2018/0133397 A1 | 5/2018 | Estes |
| 2018/0147349 A1 | 5/2018 | Finan et al. |
| 2018/0184951 A1 | 7/2018 | Varsavsky et al. |
| 2018/0185578 A1 | 7/2018 | Monirabbasi et al. |
| 2019/0035507 A1 | 1/2019 | Laguna et al. |
| 2019/0053742 A1 | 2/2019 | Steil et al. |
| 2019/0076600 A1 | 3/2019 | Grosman et al. |
| 2019/0091402 A1 | 3/2019 | Parikh et al. |
| 2019/0099555 A1 | 4/2019 | Patek et al. |
| 2019/0105444 A1 | 4/2019 | Mazlish |
| 2019/0117137 A1 | 4/2019 | Shah et al. |
| 2019/0151540 A1 | 5/2019 | Wilinska et al. |
| 2019/0167170 A1 | 6/2019 | Varsavsky et al. |
| 2019/0192764 A1 | 6/2019 | Brewer et al. |
| 2019/0231977 A1 | 8/2019 | Roy |
| 2019/0272923 A1 | 9/2019 | Duke et al. |
| 2019/0298920 A1 | 10/2019 | Haider et al. |
| 2019/0343434 A1 | 11/2019 | Varsavsky et al. |
| 2019/0357820 A1 | 11/2019 | Varsavsky et al. |
| 2019/0374137 A1 | 12/2019 | Kovatchev et al. |
| 2019/0388014 A1 | 12/2019 | Gottlieb et al. |
| 2020/0000384 A1 | 1/2020 | Desborough et al. |

FOREIGN PATENT DOCUMENTS

| | | |
|---|---|---|
| WO | WO2003022327 A2 | 3/2003 |
| WO | WO2003059422 A1 | 7/2003 |
| WO | WO2009005952 A2 | 1/2009 |
| WO | WO2009005957 A1 | 1/2009 |
| WO | WO2009005958 A2 | 1/2009 |
| WO | WO2009005960 A2 | 1/2009 |
| WO | WO2010135638 A2 | 11/2010 |
| WO | WO2011018460 A1 | 2/2011 |
| WO | WO2011018464 A1 | 2/2011 |

(56) References Cited

FOREIGN PATENT DOCUMENTS

| | | |
|---|---|---|
| WO | WO2011018465 A1 | 2/2011 |
| WO | WO2012051344 A2 | 4/2012 |
| WO | WO2012058694 A2 | 5/2012 |
| WO | WO2014008342 A1 | 1/2014 |
| WO | WO2014109898 A1 | 7/2014 |
| WO | WO2014110538 A1 | 7/2014 |
| WO | WO2015073211 A1 | 5/2015 |
| WO | WO2015088589 A1 | 6/2015 |
| WO | WO2016022650 A1 | 2/2016 |
| WO | WO2017116503 A1 | 7/2017 |
| WO | WO2017184988 A1 | 10/2017 |

* cited by examiner

CLOSED-LOOP BLOOD GLUCOSE CONTROL SYSTEMS AND METHODS

CROSS-REFERENCE TO RELATED APPLICATIONS

The present application is a National Phase entry of International Application No. PCT/EP2018/070901, filed on Aug. 1, 2018 which claims priority to and benefit of European Application No. 17306034.4, filed on Aug. 2, 2017.

FIELD OF THE INVENTION

The instant invention relates to the field of closed-loop blood glucose control system for the controlled delivery of insulin to a patient. Such systems are also known as artificial pancreas.

BACKGROUND OF THE INVENTION

An artificial pancreas is a system that automatically regulates the insulin intake of a diabetic patient based on its blood glucose history, meal history, and insulin history.

In particular, the present invention relates to Model-based Predictive Control (MPC) systems, also known as predictive control systems, in which the determination of the dose of insulin to be injected is based on a prediction of the patient's future blood glucose level obtained by computing a physiological model describing the effect of insulin in the patient's body and its impact on the patient's glucose level.

It would be desirable to be able to improve the performance of model-based artificial pancreas, and more particularly to be able to improve the accuracy of the physiological model predictions in order to better estimate insulin requirements and reduce the risk of hyperglycemia or hypoglycemia.

The instant invention has notably for object to improve this situation.

SUMMARY OF THE INVENTION

According to an aspect, the invention relates to an automated closed-loop blood glucose control system for the controlled delivery of insulin to a patient comprising:

a continuous glucose-monitoring sensor configured to provide a plurality of glucose measurement values representative of a measured glucose level of the patient at an associated plurality of measurement times;

a subcutaneous insulin delivery device configured to deliver exogenous insulin in a subcutaneous tissue of the patient in response to an insulin delivery control signal, in particular continuously infused insulin and/or bolus insulin; and a controller programmed to receive the glucose measurement values and provide a delivery control signal to the insulin delivery device, wherein the controller is able to determine a quantity of insulin to inject at at least one time step on the basis of a predicted glucose level determined by computing a physiological model of glucose-insulin system in the patient, said model comprising a system of differential equations describing the evolution of a plurality of state variables as a function of time, wherein the controller is able to compute a maximal allowable insulin injection amount and to determine the insulin delivery control signal on the basis of the maximal allowable insulin injection amount and the quantity of insulin to inject at at least one time step.

This allows improving the accuracy of the physiological model predictions.

According to some aspects, one may use one or more of the following features:

the maximal allowable insulin injection amount is computed independently from said physiological model, in particular independently of the differential equations of the physiological model describing the evolution of a plurality of state variables as a function of time;

the maximal allowable insulin injection amount is a function of a sensitivity of the patient to insulin, said sensitivity being representative of a ratio between a variation in a blood glucose level and a variation in a quantity of insulin present in the second compartment of the subcutaneous layer, said sensitivity being a decreasing function of a glucose level of the patient, in particular the maximal allowable insulin injection amount is proportional to an inverse of said sensitivity of the patient to insulin;

said sensitivity is a decreasing function of a glucose level of the patient wherein a slope of said decreasing function is smaller at an intermediate glucose level of about 100 mg/dL than at low glucose level of less than 90 mg/dL and at high glucose level of more than 180 mg/dL;

a curve relating sensitivity to glucose level is precomputed by averaging at least a plurality of simulated experiments, each simulated experiment comprises the determination of a predicted glucose level by computing a physiological model of glucose-insulin system in a patient, said physiological model includes a first sub-model of an insulin-dependent glucose absorption compartment and a second sub-model of a non-insulin-dependent glucose absorption compartment, in particular said first sub-model comprises at least one differential equation representative of a glycogenesis process and said second sub-model comprises at least one differential equation representative of a glycolysis process;

said maximal allowable insulin injection amount is a function of a predefined basal amount of continuously infused insulin and/or bolus insulin of the patient;

said predefined basal amount of continuously infused insulin is predetermined as a function of at least a mean amount of insulin consumed by a patient during a day, a mean amount of carbohydrate consumed by a patient during a day and a weight of said patient;

the maximal allowable insulin injection amount is a product of at least said predefined basal amount, a predefined personalized reactivity coefficient and an inverse of said sensitivity of the patient to insulin;

said predefined personalized reactivity coefficient is comprised between 1 and 3;

the insulin delivery control signal is determined by capping the quantity of insulin to inject at the computed maximal allowable insulin injection amount;

the system further comprises a physiological sensor adapted to measure physiological data, and the maximal allowable insulin injection amount is a function of said physiological data, Notably where the physiological sensor is a pulse monitoring sensor configured to provide a plurality of heart rate measurement values representative of a measured heart rate of the patient at an associated plurality of measurement times, and the maximal allowable insulin injection amount is a function of a heart rate of the patient, in particular a sensitivity of the patient to insulin is a function of a heart rate of the patient.

According to another aspect, the invention relates to a method for the controlled delivery of insulin to a patient using an automated closed-loop blood glucose control system, the method comprising:

continuously monitoring glucose, using a sensor, to provide a plurality of glucose measurement values representative of a measured glucose level of the patient at an associated plurality of measurement times;

determining a quantity of insulin to inject at at least one time step, using a controller, by computing a physiological model of glucose-insulin system in the patient comprising a system of differential equations describing the evolution of a plurality of state variables as a function of time, computing a maximal allowable insulin injection amount, determining an insulin delivery control signal on the basis of the maximal allowable insulin injection amount and the quantity of insulin to inject at at least one time step, and delivering exogenous insulin in a subcutaneous tissue of the patient, using a subcutaneous insulin delivery device, in accordance with said insulin delivery control signal, in particular delivering continuously infused insulin and/or bolus insulin).

According to some embodiments, one may also use one or more of the following features:

said maximal allowable insulin injection amount is computed independently from said physiological model, in particular independently of the differential equations of the physiological model describing the evolution of a plurality of state variables as a function of time;

said maximal allowable insulin injection amount is a function of a sensitivity of the patient to insulin, said sensitivity being representative of a ratio between a variation in a blood glucose level and a variation in a quantity of insulin present in the second compartment of the subcutaneous layer, said sensitivity being a decreasing function of a glucose level of the patient, in particular the maximal allowable insulin injection amount is proportional to an inverse of said sensitivity of the patient to insulin;

in the above embodiment, said sensitivity is a decreasing function of a glucose level of the patient wherein a slope of said decreasing function is smaller at a intermediate glucose level of about 100 mg/dL than at low glucose level of less than 90 mg/dL and at high glucose level of more than 180 mg/dL;

in any of the above two embodiments, a curve relating sensitivity to glucose level is pre-computed by averaging at least a plurality of simulated experiments, each simulated experiment comprises the determination of a predicted glucose level by computing a physiological model of glucose-insulin system in a patient, said physiological model includes a first sub-model of an insulin-dependent glucose absorption compartment and a second sub-model of a non-insulin-dependent glucose absorption compartment, in particular said first sub-model comprises at least one differential equation representative of a glycogenesis process and said second sub-model comprises at least one differential equation representative of a glycolysis process;

said maximal allowable insulin injection amount is a function of a predefined basal amount of continuously infused insulin and/or bolus insulin of the patient;

in the above embodiment, said predefined basal amount of continuously infused insulin is predetermined as a function of at least a mean amount of insulin consumed by a patient during a day, a mean amount of carbohydrate consumed by a patient during a day and a weight of said patient;

in any of the above two embodiments, the maximal allowable insulin injection amount is a product of at least said predefined basal amount, a predefined personalized reactivity coefficient and an inverse of said sensitivity of the patient to insulin;

in the above embodiment, said predefined personalized reactivity coefficient is comprised between 1 and 3;

the insulin delivery control signal is determined by capping the quantity of insulin to inject at the computed maximal allowable insulin injection amount;

said computing of a maximal allowable insulin injection amount is periodically performed.

BRIEF DESCRIPTION OF THE DRAWINGS

Other characteristics and advantages of the invention will readily appear from the following description of several of its embodiments, provided as non-limitative examples, and of the accompanying drawings.

On the drawings.

On the different figures, the same reference signs designate like or similar elements.

DETAILED DESCRIPTION

For the sake of clarity, only elements which are useful for understanding the embodiments described are shown on the figures and detailed in the present description. In particular, the glucose-monitoring sensor and the insulin delivery device of the blood glucose control system are not specifically detailed since the embodiments of the present invention are compatible with all or a majority of the blood glucose measuring and insulin injection devices.

Physical embodiments of the controller of the described control system are also not described with excessive details, the realization of such a controller unit being within the scope of the skilled man given the functional explanations given in the present specification.

Figure 1:
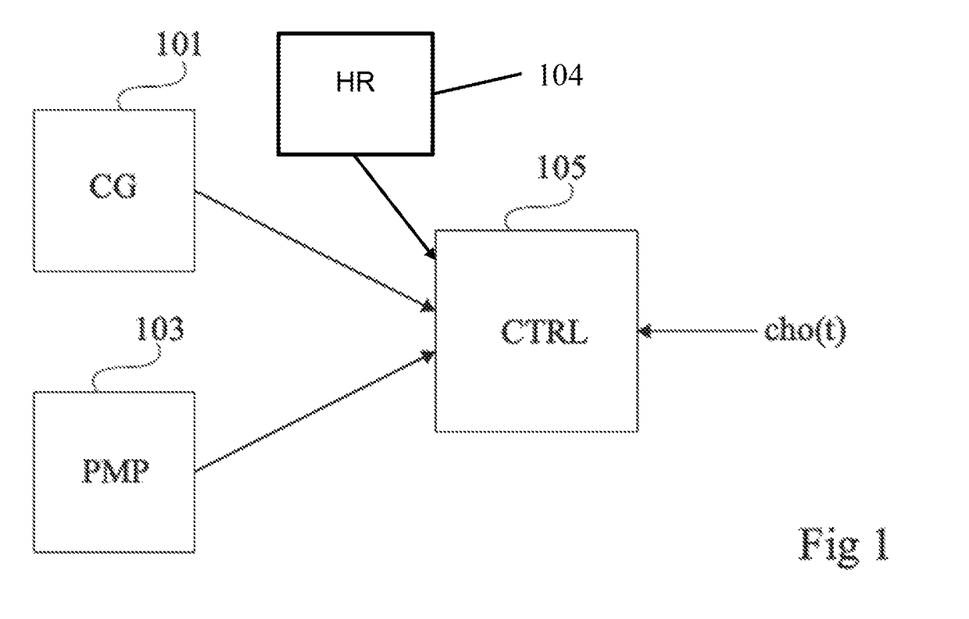
FIG. 1 schematically illustrates, in the form of a block diagram, an embodiment of an automated closed-loop blood glucose control system for the controlled delivery of insulin to a patient according to the invention.

FIG. 1 illustrates an example of an embodiment of an automated closed-loop blood glucose control system for the controlled delivery of insulin to a patient, in the form of a block diagram.

The system of FIG. 1 comprises a sensor 101 (CG) adapted to measure the blood glucose level of the patient. In normal operation, the sensor 101 can be positioned permanently on or in the body of the patient, for example at the level of its abdomen. The sensor 101 is for example a sensor of the "Continuous Glucose Monitoring" type (CGM), that is to say a sensor adapted to measure continuously (for example at least once per minute) the patient's blood glucose level. The sensor 101 is, for example, a subcutaneous blood glucose sensor.

The sensor may for instance comprise a disposable glucose sensor placed just under the skin, which may be worn for a few days and periodically replaced.

During the operation of the method and system of the present invention, the sensor 101 provides a plurality of glucose measurement values representative of a measured glucose level of the patient at an associated plurality of measurement times.

In the present description, "glucose level" is understood as a concentration of glucose in the blood, also called glycemia.

The system of FIG. 1 further comprises an insulin delivery device 103 (PMP), for example a subcutaneous injection device. The device 103 is for example an automatic injection device, like an insulin pump, comprising an insulin reservoir connected to an injection needle implanted under the skin of the patient. The pump is electrically commanded to inject controlled doses of insulin at determined times. In normal operation, the injection device 103 is positioned in or on the body of the patient, for example at the level of its abdomen.

During the operation of the method and system of the present invention, the insulin delivery device 103 delivers exogenous insulin in the subcutaneous tissue of the patient in response to an insulin delivery control signal. The exogenous insulin is in particular rapid-acting insulin. Rapid-acting insulin can be delivered by the insulin delivery device in two ways:

a bolus dose that is delivered to cover food eaten or to correct a high blood glucose level, or a basal dose that is pumped continuously at an adjustable basal rate to deliver insulin needed between meals and at night.

In some embodiments, the system may also comprise a pulse monitoring sensor 104. The pulse monitoring sensor 104 is able to provide a plurality of heart rate measurement values h(t) representative of a heart rate of the patient measured at an associated plurality of measurement times. The pulse monitoring sensor 104 can be provided on an armband or waistband, for example. The sensor can be wirelessly connected to the remote controller 105 for the transfer of measured data thereto.

Alternatively, one may use another physiological sensor than a pulse monitoring sensor. Typical examples include a sensor measuring the electrical conductivity or the superficial temperature of the skin.

As illustrated on FIG. 1, the system further comprises a controller 105 (CTRL) which is a controller 105 connected to the glucose-monitoring sensor 101 and to the insulin delivery device 103 and, optionally, to the pulse monitoring sensor 104, for example by wired or radio (wireless) links.

During the operation of the method and system of the present invention, the controller 105 receives the blood glucose data of the patient measured by the sensor 101 and provides the delivery control signal to the insulin delivery device. The controller 105 may further receive, via a non-detailed user interface, indication of an amount of glucose ingested by the patient.

Such an indication on the amount of glucose is referenced as cho(t) and is in particular representative of the evolution of the ingestion of carbohydrate by the patient.

The controller 105 is adapted to determine the insulin delivery control signal to provide to the insulin delivery device.

To this aim, the controller 105 comprises a digital calculation circuit (not detailed), comprising, for example, a microprocessor. The controller 105 is, for example, a mobile device carried by the patient throughout the day and/or at night. One possible embodiment of the controller 105 may be a smartphone device configured to implement a method as described hereinafter.

The controller 105 is in particular adapted to determine a quantity of insulin to inject at at least one time step, taking into account a prediction of the future evolution of a blood glucose level of the patient as a function of time.

More precisely, the controller 105 determine a quantity of insulin to inject at at least one time step on the basis of a predicted glucose level determined by computing a physiological model of glucose-insulin system in the patient.

Figure 4:
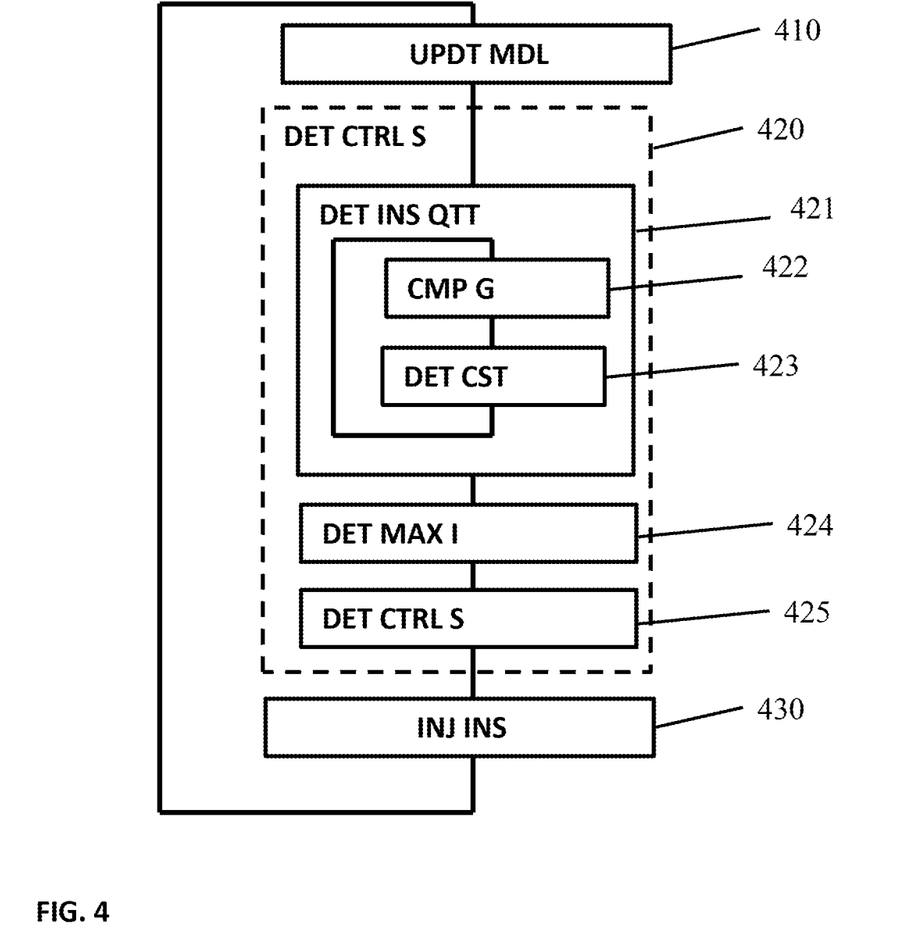
FIG. 4 is a diagram illustrating an example of a method for the controlled delivery of insulin to a patient using the automated closed-loop blood glucose control system of FIG. 1.

This determination operation is performed during an operation 420 illustrated on FIG. 4.

The controller 105 thus determines a curve representative of an expected evolution of the patient's glucose level as a function of time over a future period.

Taking this curve into account, the controller 105 determines the doses of insulin to be injected to the patient during the next period so that the glucose level of the patient remains within an acceptable range to limit the risk of hyperglycemia or hypoglycemia. As explained hereinafter, the glucose measurement values measured by the sensor 101 may for instance be used to perform a self-calibration operation of the physiological model.

Figure 2:
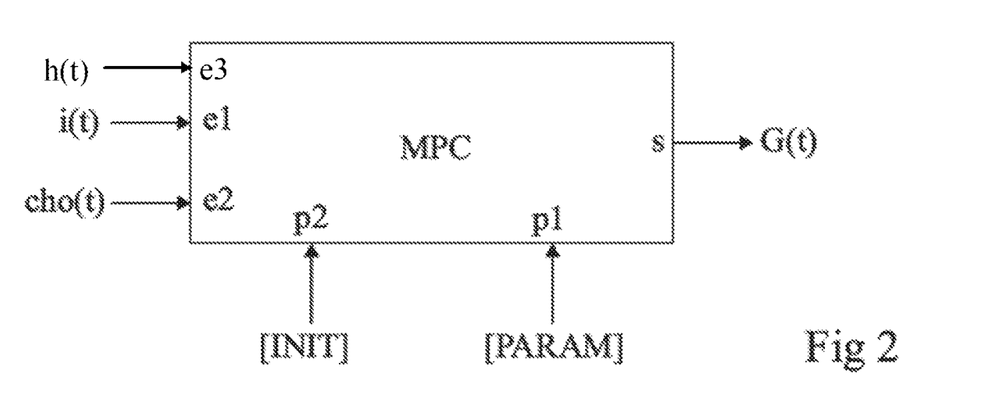
FIG. 2 is a simplified representation of a physiological model used in the system of FIG. 1 to predict blood glucose level of a patient.

FIG. 2 is a schematic illustration of a physiological model of glucose-insulin system that may be implemented in the system of FIG. 1 to predict the evolution of glucose level of the patient.

The model is represented on FIG. 2 as a processing block comprising:

an input e1 on which is applied a signal i(t) indicative of an evolution, as a function of time t, of a quantity of exogenous insulin delivered in a subcutaneous layer of the patient by the insulin delivery device;

an input e2 on which is applied a signal cho(t) indicative of the evolution, as a function of time t, of the amount of glucose ingested by the patient, for example a quantity of carbohydrate ingested during a meal at a given time;

an input e3 on which is applied a signal h(t) indicative of the evolution, as a function of time t, of the heart rate of the patient; and an output s providing a signal G(t) representative of the evolution, as a function of time t, of the patient's glucose level.

According to some embodiments, other physiological signals than the heart rate can be provided as input e3, as disclosed above.

The physiological model MPC is for example a compartmental model comprising, in addition to the input variables i(t) and cho(t) and the output variable G(t), a plurality of state variables corresponding to the instantaneous values of a plurality of physiological variables of the patient as they evolves over time.

The temporal evolution of the state variables is governed by a system of differential equations comprising a plurality of parameters represented in FIG. 2 by a vector [PARAM] applied to an input p1 of the MPC block.

The response of the physiological model may also be conditioned by the initial values assigned to the state variables, which is represented on FIG. 2 by a vector [INIT] applied to an input p2 of the MPC block.

Figure 3:
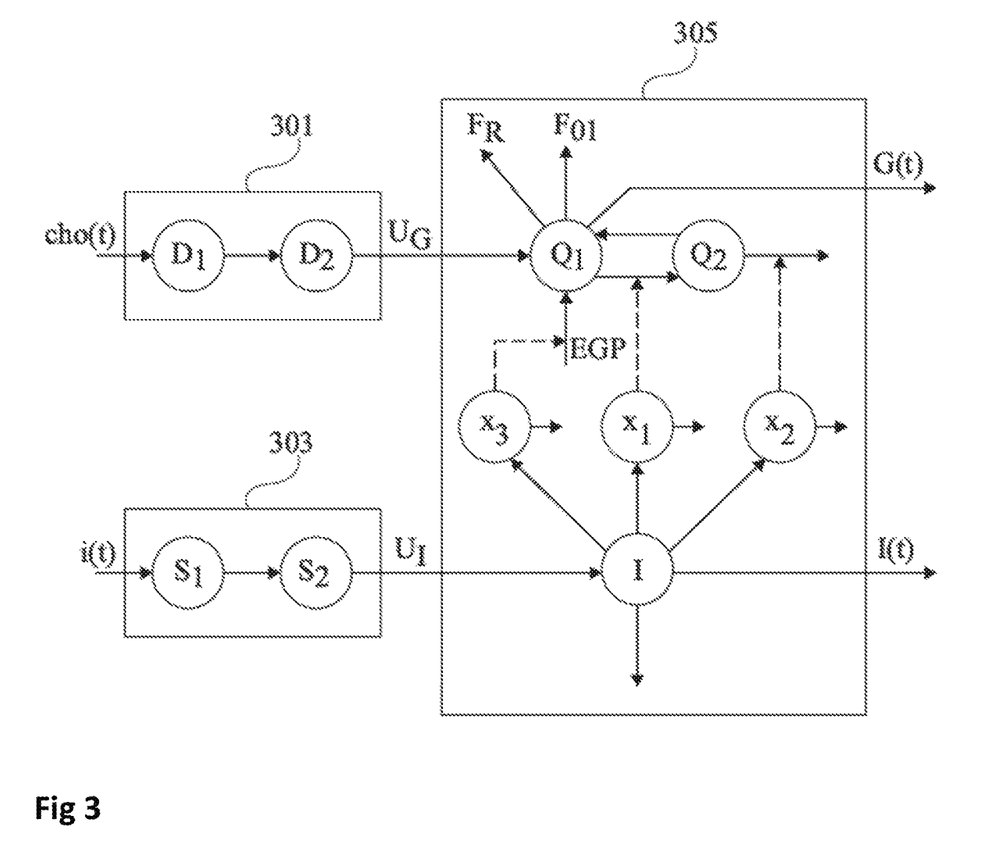
FIG. 3 is a diagram representing in greater detail an embodiment of the physiological model of FIG. 2.

FIG. 3 is a diagram which represents in greater detail a non-limiting example of a physiological model implemented in an embodiment of the system of FIG. 1.

This exemplary model is known as the Hovorka model and is described for instance in "Nonlinear model predictive control of glucose concentration in subjects with type 1 diabetes" by Roman Hovorka et al. (Physiol Meas., 2004; 25: 905-920) and in "Partitioning glucose distribution/transport, disposal, and endogenous production during IVGTT" by Roman Hovorka et al. (Physical Endocrinol Metab 282: E992-E1007, 2002).

The physiological model illustrated on FIG. 3 comprises a first bi-compartmental sub-model 301 describing the effect of glucose intake on the rate of onset of glucose in blood plasma.

Sub-model 301 takes as input a quantity of ingested glucose cho(t), for example in mmol/min, and provides as an output a rate $U_G$ of absorption of glucose in the blood plasma, for example in mmol/min.

In this model, sub-model 301 comprises two state variables $D_1$ and $D_2$ that respectively corresponds to glucose masses, for example in mmol, respectively in the first and the second compartment.

The model of FIG. 3 also comprises a second bi-compartmental sub-model 303 describing the absorption of exogenous insulin delivered to the patient in the blood plasma. Sub-model 303 takes a quantity of exogenous insulin i(t) delivered in the subcutaneous tissue of the patient as an input, for example in mU/min, and provides as an output a rate $U_I$ of absorption of insulin in the plasma, in MU/min.

The sub-model 303 may for instance comprise two state variables $S_1$ and $S_2$, respectively corresponding to on-board insulin which are insulin masses respectively in the first and the second compartments modeling a subcutaneous compartment representative of the sub-cutaneous tissue of the patient. The instantaneous on-board insulin level of the state variables $S_1$ and $S_2$ may for example be expressed in mmol.

The model of FIG. 3 may further comprise a third sub-model 305 describing the regulation of glucose by the patient's body. This sub-model 305 takes as inputs the absorption rates $U_G$, $U_I$ of glucose and insulin, and gives as output the blood glucose level G(t), i.e. the concentration of glucose in the plasma, for example in mmol/l.

The sub-model 305 is thus a model of a plasma/body compartment of the patient, i.e. a model of the kinetic and chemical evolution of glucose and insulin in the plasma and the body of the patient.

By "plasma and body of the patient", it is meant the body of the patient with the exception of the sub-cutaneous tissues.

In this example, the submodel 305 comprises six state variables Q1, Q2, x3, x1, x2, I.

Variables Q1 and Q2 respectively correspond to masses of glucose respectively in the first and the second compartments, for example mmol.

Variables x1, x2, x3 are dimensionless variables respectively representing each of three respective actions of insulin on the kinetics of glucose.

Finally, variable I is an instantaneous plasma insulin level, i.e. corresponds to insulinemia which is a concentration of insulin in the blood plasma. The instantaneous plasma insulin level is for example expressed in mU/l.

The Hovorka model is governed by the following system of equations:

$$\frac{dS_1}{dt} = i(t) - k_a \cdot S_1(t)$$

$$\frac{dS_2}{dt} = k_a \cdot S_1(t) - k_a \cdot S_2(t)$$

$$\frac{dI}{dt} = \frac{k_a \cdot S_2(t)}{V_I} - k_e \cdot I(t)$$

$$\frac{dD_1}{dt} = cho(t) - \frac{D_1(t)}{t_{max}}$$

$$\frac{dD_2}{dt} = \frac{D_1(t)}{t_{max}} - \frac{D_2(t)}{t_{max}}$$

$$U_G = \frac{D_2(t)}{t_{max}}$$

$$\frac{dQ_1}{dt} = -\left[\frac{F_{01}^c}{V_G \cdot G(t)} + x_1(t)\right] \cdot Q_1(t) + k_{12}Q_2(t) - F_R + EGP_0 \cdot [1 - x_3(t)] + U_G(t)$$

$$\frac{dQ_2}{dt} = x_1(t) \cdot Q_1(t) - [k_{12} + x_2(t)] \cdot Q_2(t)$$

$$\frac{dx_1}{dt} = -k_{a1} \cdot x_1(t) + k_{b1} \cdot I(t)$$

$$\frac{dx_2}{dt} = -k_{a2} \cdot x_2(t) + k_{b2} \cdot I(t)$$

$$\frac{dx_3}{dt} = -k_{a3} \cdot x_3(t) + k_{b3} \cdot I(t)$$

$$G(t) = \frac{Q_1(t)}{V_G}$$

with $$F_{01}^c = \frac{F_{01} \cdot G(t)}{0.85 \cdot (G(t) + 1 \ldots 0)} \text{ and}$$

$$F_R = \begin{cases} 0.003 (G-9) \cdot V_G & \text{if } G > 9 \\ 0 & \text{else} \end{cases}$$

This system of differential equations comprises fifteen parameters $V_G$, $F_{01}$, $k_{12}$, $F_R$, $EGP_0$, $k_{b1}$, $k_{a1}$, $k_{b2}$, $k_{a2}$, $k_{b3}$, $k_{a3}$, $k_a$, $V_I$, $k_e$ and $t_{max}$ with the following meaning:

$V_G$ corresponds to a volume of distribution of the glucose, for example in liters, $F_{01}$ corresponds to a non-insulin-dependent glucose transfer rate, for example in mmol/min, $k_{12}$ corresponds to a transfer rate between the two compartments of sub Model 305, for example in $min^{-1}$, $k_{a1}$, $k_{a2}$, $k_{a3}$ correspond to an insulin deactivation rate constants, for example in $min^{-1}$, $F_R$ corresponds to a urinary excretion of glucose, for example in mmol/min, $EGP_0$ corresponds to an endogenous production of glucose, for example in $min^{-1}$, $k_{b1}$, $k_{b2}$ and $k_{b3}$ correspond to insulin activation rate constants, for example in $min^{-1}$, $k_a$ corresponds to a rate of absorption of the insulin injected subcutaneously, for example in min−1, $V_I$ corresponds to the volume of distribution of the insulin, for example in liters, $k_e$ corresponds to a plasma elimination rate of insulin, for example in $min^{-1}$, and $t_{max}$ corresponds to a time to peak glucose absorption ingested by the patient, for example in min.

These fifteen parameters correspond to the vector [PARAM] illustrated on FIG. 2.

This model further comprises ten state variables $D_1$, $D_2$, $S_1$, $S_2$, $Q_1$, $Q_2$, $x_1$, $x_2$, $x_3$ and I, which are initiated to a vector

[INIT] of initial values corresponding to values of these variables at a time step t0 corresponding a beginning of the simulation of the patient's behavior by the model.

The system and method of the invention may also uses more simple physiological models than the Hovorka model described above, in particular a compartmental model with a smaller number of state variables and a reduced number of parameters compared to the Hovorka model.

In some embodiment of the invention, several physiological models may be stored in the controller and the predictions of said models may be compared together or may be used independently, for example depending on a state of the controller or a confidence indicator that may be computed for the predictions of said models.

In particular, the embodiments described are not limited to the Hovorka physiological model but are compatible with any physiological model describing the assimilation of insulin by a patient's body and its effect on the patient's blood glucose level.

One example of another physiological model is the Cobelli model described in "A System Model of Oral Glucose Absorption: Validation on Gold Standard Data" by Chiara Dalla Man et al. in IEEE TRANSACTIONS ON BIOMEDICAL ENGINEERING, VOL 53, NO 12, DECEMBER 2006.

Such models are known from the literature.

In these models, the absorption rate of insulin from the subcutaneous tissue to the plasma is constant.

There is such a need to improve the accuracy of predicting the absorption of insulin from the subcutaneous tissue to the plasma.

Using the above described model, the controller 105 perform can determine an insulin delivery control signal by performing a cost optimization operation.

The cost optimization operation advantageously comprises a plurality of prediction steps for a plurality of respective tested insulin injection.

A tested insulin injection is a set comprising at least one value indicative of a quantity of insulin injected at a future time. The tested insulin injection may comprise a plurality of M values indicative of a quantity of insulin injected at a respective future time of a plurality of M future time step, with M being an integer strictly greater than 1.

A prediction step 421 for a tested insulin injection comprises the sub-steps of:

computing 422 a plurality of predicted glucose levels at a plurality of respective future time steps by unrolling the physiological model over time, and determining 423 a cost associated to said plurality of predicted glucose levels.

The unrolling of the physiological model over time is performed using the tested insulin injection and a set of pre-estimated model parameters that can be in particular determined during a self-calibration operation as detailed further below.

The cost associated to the predicted glucose levels is for instance related to a distance of each predicted glucose level with a target glucose level.

The target glucose level may be pre-defined and personalized for the patient. The target glucose level may be comprised between 100 and 130 mg/dL.

The cost function can be for example a quadratic function of a difference between a predicted glucose level and a target glucose level.

Advantageously, the cost function may be asymmetrical and in particular may penalize more strongly glucose level lower than the target glucose level than glucose level higher than the target glucose level.

In some embodiment of the invention, the cost associated to the predicted glucose levels is a function of a time-restricted subset of the plurality of predicted glucose levels.

Such a time-restricted subset may be such that the predicted glucose levels are only considered in a restricted range, in which the glucose level of the patient may be considered controllable by the system and method of the invention.

For example, glucose level in a short future period close to the current time may not be considered controllable since the kinetic of sub-cutaneous delivered insulin is too slow to have an effect in the near future. On the other hand, glucose level in a far future period, far-away from the current time, may also not be considered controllable since the uncertainty on the parameters, states-variables and meal uptake is too high to have a reliable prediction of the glucose level.

Thus, a first predicted glucose level of said time-restricted subset may be associated to a first time step not closer than 30 minutes from a current time step and a last predicted glucose level of said time-restricted subset may be associated to a last time step not further than 3 hours from a current time step.

The controller can thus determine a quantity of insulin to inject by performing a cost optimization operation comprising a plurality of prediction steps 421 for a plurality of respective tested insulin injection as illustrated on FIG. 4.

The controller 105 may in particular select a quantity of insulin to inject minimizing the cost associated to the predicted glucose levels.

The controller 105 can then determine an insulin delivery control signal as follows.

First, the controller 105 may compute a maximal allowable insulin injection amount $i_{max}$ during a step 424.

The maximal allowable insulin injection amount is computed independently from the physiological model. In particular, the maximal allowable insulin injection amount is computed without unrolling the differential equations of the physiological model.

This increase the reliance of the system and method of the invention by reducing correlated errors arising from the simulation of the physiological model.

In one embodiment of the invention, the maximal allowable insulin injection amount $i_{max}$ is a function of a sensitivity $S_I$ of the patient to insulin.

The maximal allowable insulin injection amount may for instance be proportional to an inverse of said sensitivity of the patient to insulin.

The sensitivity $S_I$ of the patient to insulin is representative of a ratio between a variation in a blood glucose level and a variation in a quantity of insulin present in the second compartment of the subcutaneous layer:

$$S_I = \frac{dG}{dS_2}$$

The sensitivity $S_I$ may in particular be a decreasing function of the blood glucose level G of the patient.

The sensitivity $S_I$ is a function of a glucose level of the patient such as the slope of said decreasing function is smaller at an intermediate glucose level of about 100 mg/dL than at low glucose level of less than 90 mg/dL and at high glucose level of more than 180 mg/dL.

Such a curve may be pre-computed and stored in a memory of the controller 105. The curve may be computed in the following way.

A plurality of simulated experiments can be conducted. Each simulated experiment involve the computation of a physiological model of glucose-insulin system in a patient to determine a predicted glucose level. A plurality of ratio of variations of the predicted glucose level to variations of the sub-cutaneous quantity of insulin may be computed from each simulated experiment.

The physiological model includes in particular a first sub-model of an insulin-dependent glucose absorption compartment and a second sub-model of a non-insulin-dependent glucose absorption compartment.

Thus, the first sub-model comprises for example a differential equation representative of a glycogenesis process while the second sub-model comprises for example a differential equation representative of a glycolysis process.

The curve relating the sensitivity $S_I$ to the blood glucose level G of a patient may then be computed by averaging the plurality of experiments.

In addition, in-vivo experiments may be conducted to measure a plurality of glucose levels and sub-cutaneous quantity of insulin. Thus, a plurality of ratio between variations of blood glucose level and variations of the sub-cutaneous quantity of insulin may also be determined from in-vivo experiments. The in-vivo experiments and the simulated experiments may be averaged together to determine a curve relating the sensitivity $S_I$ to the blood glucose level G.

The maximal allowable insulin injection amount $i_{max}$ may also be a function of a predefined basal amount of continuously infused insulin and/or bolus insulin of the patient $i_{basal}$.

The predefined basal amount of continuously infused insulin $i_{basal}$ can be predetermined for a given patient, for example pre-computed by a physician. The basal amount of continuously infused insulin $i_{basal}$ is for example a function of a mean amount of insulin consumed by a patient during a day, a mean amount of carbohydrate consumed by a patient during a day and a weight of said patient.

More generally, the maximal allowable insulin injection amount $i_{max}$ can thus for example be a product of at least said predefined basal amount, a predefined personalized reactivity coefficient and an inverse of said sensitivity of the patient to insulin:

$$i_{max} = \frac{r_{norm} \cdot i_{basal}}{S_I}$$

where $r_{norm}$ is a predefined personalized reactivity coefficient.

The personalized reactivity coefficient $r_{norm}$ is typically comprised between 1 and 3 and can be adjusted dynamically. This way, it is possible to adjust the responsiveness of the system and method of the invention.

When the system comprises a pulse monitoring sensor, the maximal allowable insulin injection amount may also be a function of a heart rate of the patient h(t).

In one example, the sensitivity of the patient to insulin is thus a function of a heart rate of the patient. In particular, the sensitivity of the patient to insulin may decrease as the patient's heart rate increases.

According to some embodiments, the sensitivity of the patient to insulin may be a function of other physiological signals than the heart rate, as disclosed above.

Once the maximal allowable insulin injection amount has been computed, the controller 105 can determine 425 the insulin delivery control signal for example by capping the quantity of insulin to inject at the computed maximal allowable insulin injection amount.

This reduces the risk of unrealistic prediction from the model, in particular when there is a high level of noise or uncertainty for some of the current parameters. It is thus possible to ensure that the signal send to the delivery device is always in a reasonable range of values that is function of pre-determined parameters independent of the physiological model 4.

The delivery device can then inject insulin 430 on the basis of the delivery control signal.

Among the parameters of the [PARAM] vector, some parameters may be considered as constant for a given patient, for example parameters $k_{12}$, $k_{a1}$, $k_{a2}$, $k_{a3}$, $k_a$, $k_e$, $V_I$, $V_G$ and $t_{max}$. Other parameters, referred to hereinafter as time-dependent parameters, may change over time, for example the parameters $k_{b1}$, $k_{b2}$, $k_{b3}$, $EGP_0$, $F_{01}$ and $F_R$.

Because of this variation of some parameters, it is in practice necessary to regularly recalibrate or self-calibration the model in use, for example every 1 to 20 minutes, to ensure that the predictions remain accurate.

The self-calibration of the model should advantageously be carried out automatically by the system, in particular without physically measuring the parameters of the model.

FIG. 4 is a diagram illustrating an example of a method according to the invention.

This method comprises an operation 410 of self-calibration of the model, which may for example be repeated at regular intervals, for example every 1 to 20 minutes.

Figure 5:
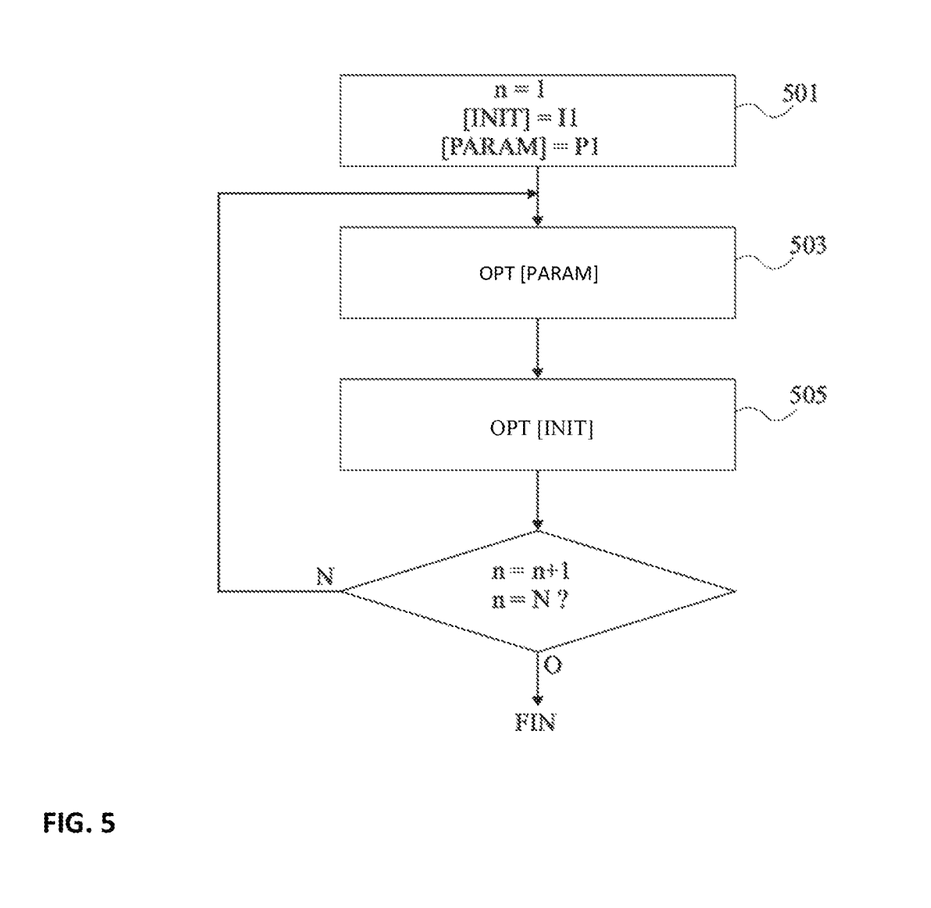
FIG. 5 is an explanatory diagram for an embodiment of the self-calibration operation.

This self-calibration operation is illustrated in greater detail on FIG. 5.

During this self-calibration operation, the controller 105 implements a determination of a set of pre-estimated model parameters taking into account the glucose measurement values, known insulin delivery control signals and at least one meal ingestion indicator during a past period, for example a period of 1 to 10 hours preceding the self-calibration operation.

For example, during the self-calibration operation, the controller 105 may simulates the behavior of the patient over the past period using the physiological model and taking into account glucose ingestions and exogenous insulin injections during this period. The controller 105 may then compares the glucose level curve estimated using the model to the actual glucose measurements by the sensor over the same period.

The controller 105 may then determine a set of pre-determined values for a set of model parameters that leads to minimizing a cost function over the observation period.

In a similar manner, the self-calibration operation may comprise an estimation of the initial states vector [INIT] of the state variables of the model, as it will now be described in relation with FIG. 5 which is illustrating an example of an embodiment of a method according to the invention.

The self-calibration operation comprises a step 501 during which a set of parameters of the model is initialized to a first set of values P1 of the parameter vector [PARAM].

The set P1 corresponds, for example, to the values taken by the parameters [PARAM] during a previous self-calibration operation. In a variant, the set of values P1 may be a predefined reference set corresponding, for example, to mean values of the parameters [PARAM] over a reference period.

During a step 501, a set of state variables values may also be initialized to a first set of values I1 forming an initial state vector [INIT].

The set of values I1 may be determined analytically, for example by assuming a stationary state of the patient in a period preceding the calibration phase and coinciding an estimated blood glucose level at time t0 with an actual glucose level measurement at that time.

In a subsequent step 503, the controller 105 may fix the set of initial states [INIT] to its current state and search for a set of values for the parameters of the model to minimizing a cost, for example an error between an estimated glucose level curve predicted by the model and an actual glucose level curve during a past observation period.

An example of such a cost function may be written as:

$$m = \frac{1}{\Delta T} \sum_{t=t_0}^{t_0+\Delta T} |g(t) - \hat{g}(t)|^2$$

where t is a discretized time, $t_0$ correspond to an initial time of the past observation period, $t_0+\Delta T$ correspond to an end of said past observation period (for instance the beginning of the self-calibration operation), g(t) is a curve determined from the glucose level measurements and ĝ(t) is a curve determined from the glucose level predicted by the model.

At the end of this step, the [PARAM] vector is updated with the new estimated values.

In a step 505 subsequent to step 503, the controller 105 then searches for a set of initial state values, setting the parameter set [PARAM] to its current state, here again by minimizing a cost such as the above described error between the estimated glucose level curve predicted by the model and an actual glucose level curve determined during a past observation period.

At the end of this step, the vector [INIT] is updated with the new estimated values.

In some embodiments, steps 503 and 505 may be reiterated a number N of times, where N is an integer greater than 1 that may be predetermined.

The values of the parameters and the initial states of the model are then updated to the corresponding values of the vectors [PARAM] and [INIT] at the end of the Nth iteration of steps 503 and 505.

In a variant, the number of iterations of steps 503 and 505 may not be predetermined and may be adjusted by taking into account the evolution of cost function over the successive iterations.

The algorithms that can be used to find the optimal values in steps 503 and 505 are not described in details in the present application. The method described in the present specification is compatible with the algorithms commonly used in various domains to solve optimization problems by minimizing a cost function.

The invention claimed is:
1. An automated closed-loop blood glucose control system for the controlled delivery of insulin to a patient, wherein the control system comprises:
a continuous glucose-monitoring sensor configured to provide a plurality of glucose measurement values representative of a measured glucose level of the patient at an associated plurality of measurement times;
a subcutaneous insulin delivery device configured to deliver exogenous insulin in a subcutaneous tissue of the patient in response to an insulin delivery control signal, in particular continuously infused insulin and/or bolus insulin; and
a controller programmed to receive the glucose measurement values and provide a delivery control signal to the insulin delivery device,
wherein the controller is able to determine a quantity of insulin to inject at at least one time step on the basis of a predicted glucose level determined by computing a physiological model of glucose-insulin system in the patient, said model comprising a system of differential equations describing the evolution of a plurality of state variables as a function of time,
wherein the controller is able to compute a maximal allowable insulin injection amount and to determine the insulin delivery control signal on the basis of the maximal allowable insulin injection amount and the quantity of insulin to inject at at least one time step,
wherein the maximal allowable insulin injection amount is a function of a sensitivity of the patient to insulin,
said sensitivity being representative of a ratio between a variation in a blood glucose level and a variation in a quantity of insulin present in a second compartment of the subcutaneous layer,
said sensitivity being a decreasing function of a glucose level of the patient,
wherein the maximal allowable insulin injection amount is proportional to an inverse of said sensitivity of the patient to insulin.
2. The system according to claim 1, wherein the maximal allowable insulin injection amount is computed independently from the differential equations of the physiological model describing the evolution of a plurality of state variables as a function of time.
3. The system according to claim 1, wherein said sensitivity is a decreasing function of a glucose level of the patient wherein a slope of said decreasing function is smaller at an intermediate glucose level of about 100 mg/dL than at low glucose level of less than 90 mg/dL and at high glucose level of more than 180 mg/dL.
4. The system according to claim 1, wherein a curve relating sensitivity to glucose level is precomputed by averaging at least a plurality of simulated experiments,
wherein each simulated experiment comprises the determination of a predicted glucose level by computing a physiological model of glucose-insulin system in a patient,
wherein said physiological model includes a first sub-model of an insulin-dependent glucose absorption compartment and a second sub-model of a non-insulin-dependent glucose absorption compartment,
in particular wherein said first sub-model comprises at least one differential equation representative of a glycogenesis process and said second sub-model comprises at least one differential equation representative of a glycolysis process.
5. The system according to claim 1, wherein said maximal allowable insulin injection amount is a function of a predefined basal amount of continuously infused insulin and/or bolus insulin of the patient.
6. The system according to claim 5, wherein said predefined basal amount of continuously infused insulin is predetermined as a function of at least a mean amount of insulin consumed by a patient during a day, a mean amount of carbohydrate consumed by a patient during a day and a weight of said patient.

7. The system according to claim 5, wherein the maximal allowable insulin injection amount is a product of at least said predefined basal amount, a predefined personalized reactivity coefficient and an inverse of said sensitivity of the patient to insulin.

8. The system according to claim 7, wherein said predefined personalized reactivity coefficient is comprised between 1 and 3.

9. The system according to claim 1, wherein the insulin delivery control signal is determined by capping the quantity of insulin to inject at the computed maximal allowable insulin injection amount.

10. The system according to claim 1, wherein the system further comprises a physiological sensor adapted to measure physiological data, and wherein the maximal allowable insulin injection amount is a function of said physiological data, notably where the physiological sensor is a pulse monitoring sensor configured to provide a plurality of heart rate measurement values representative of a measured heart rate of the patient at an associated plurality of measurement times, and wherein the maximal allowable insulin injection amount is a function of a heart rate of the patient, in particular wherein a sensitivity of the patient to insulin is a function of a heart rate of the patient.

11. A method for the controlled delivery of insulin to a patient using an automated closed-loop blood glucose control system, wherein the method comprises:

continuously monitoring glucose, using a sensor, to provide a plurality of glucose measurement values representative of a measured glucose level of the patient at an associated plurality of measurement times;

determining a quantity of insulin to inject at at least one time step, using a controller, by computing a physiological model of glucose-insulin system in the patient comprising a system of differential equations describing the evolution of a plurality of state variables as a function of time, computing a maximal allowable insulin injection amount, determining an insulin delivery control signal on the basis of the maximal allowable insulin injection amount and the quantity of insulin to inject at at least one time step, and delivering exogenous insulin in a subcutaneous tissue of the patient, using a subcutaneous insulin delivery device, in accordance with said insulin delivery control signal, in particular delivering continuously infused insulin and/or bolus insulin, wherein said maximal allowable insulin injection amount is a function of a sensitivity of the patient to insulin, said sensitivity being representative of a ratio between a variation in a blood glucose level and a variation in a quantity of insulin present in a second compartment of the subcutaneous layer, said sensitivity being a decreasing function of a glucose level of the patient, wherein the maximal allowable insulin injection amount is proportional to an inverse of said sensitivity of the patient to insulin.

12. The method according to claim 11, wherein said maximal allowable insulin injection amount is computed independently of the differential equations of the physiological model describing the evolution of a plurality of state variables as a function of time.

13. The method according to claim 11, wherein the insulin delivery control signal is determined by capping the quantity of insulin to inject at the computed maximal allowable insulin injection amount.

14. An automated closed-loop blood glucose control system for the controlled delivery of insulin to a patient, wherein the control system comprises:

a continuous glucose-monitoring sensor configured to provide a plurality of glucose measurement values representative of a measured glucose level of the patient at an associated plurality of measurement times;

a subcutaneous insulin delivery device configured to deliver exogenous insulin in a subcutaneous tissue of the patient in response to an insulin delivery control signal, in particular continuously infused insulin and/or bolus insulin; and a controller programmed to receive the glucose measurement values and provide a delivery control signal to the insulin delivery device, wherein the controller is able to determine a quantity of insulin to inject at at least one time step on the basis of a predicted glucose level determined by computing a physiological model of glucose-insulin system in the patient, said model comprising a system of differential equations describing the evolution of a plurality of state variables as a function of time, wherein the controller is able to compute a maximal allowable insulin injection amount and to determine the insulin delivery control signal on the basis of the maximal allowable insulin injection amount and the quantity of insulin to inject at at least one time step, wherein said maximal allowable insulin injection amount is a function of a predefined basal amount of continuously infused insulin and/or bolus insulin of the patient, and wherein the maximal allowable insulin injection amount is a product of at least said predefined basal amount, a predefined personalized reactivity coefficient and an inverse of said sensitivity of the patient to insulin.

* * * * *